United States Patent [19]

Cozean, Jr.

[11] 4,441,217
[45] Apr. 10, 1984

[54] INTRAOCULAR LENSES

[76] Inventor: Charles H. Cozean, Jr., 937 Broadway, Cape Girardeau, Mo. 63701

[21] Appl. No.: 332,533

[22] Filed: Dec. 21, 1981

[51] Int. Cl.³ ............................ A61F 1/16; A61F 1/24
[52] U.S. Cl. ................................................................ 3/13
[58] Field of Search ........................................ 3/13, 1

[56] References Cited

U.S. PATENT DOCUMENTS

| | | | |
|---|---|---|---|
| 4,014,049 | 3/1977 | Richards et al. | 3/13 |
| 4,092,743 | 6/1978 | Kelman | 3/13 |
| 4,174,543 | 11/1979 | Kelman | 3/13 |
| 4,253,200 | 3/1981 | Kelman | 3/13 |
| 4,257,130 | 3/1981 | Bayers | 3/13 |
| 4,340,979 | 7/1982 | Kelman | 3/13 |
| 4,370,760 | 2/1983 | Kelman | 3/13 |

*Primary Examiner*—Ronald L. Frinks
*Attorney, Agent, or Firm*—Hubbard, Thurman, Turner & Tucker

[57] ABSTRACT

A method of correcting aphakic conditions in human eyes and a novel intraocular lens structure for accomplishing such are disclosed wherein the lens structure has a light focusing lens body with oppositely disposed support members for supporting the lens structure upon implantation in the eye. The oppositely disposed support members contact natural regions of the eye and position the optical axis of the light focusing lens at a point that is offset from the geometric center axis of the cornea whereby the optical axis corresponds with and is aligned with the pupillary axis of the eye.

9 Claims, 11 Drawing Figures

RIGHT EYE

RIGHT EYE

LEFT EYE

INTRAOCULAR LENSES

BACKGROUND OF THE INVENTION

This invention relates to improved intraocular lenses. In another aspect, the invention relates to an improved method for restoring or improving vision in humans by the implantation of intraocular lenses.

When the natural lens of an eye is removed, a condition known as an aphakic condition results. Such a condition is caused by the intracapsular or extracapsular lens extraction of the natural lens of the eye. As a result, the eye does not have the ability to focus on rays of light. Therefore, the eye receives a blurred image and vision is severely impaired.

Throughout the past several years, many different methods and apparatus have been suggested to correct aphakic conditions. For example, contact lenses, spectacles or a combination thereof have been utilized. Such methods and apparatus have only met with limited success because such solutions to the problem pose many problems. For example, spectacles that are used to correct aphakic conditions have been found to remarkably increase the size of familiar articles. Therefore, it may take many weeks for a patient to adjust to the condition of wearing spectacles. Additionally, the wearer of such spectacles experiences problems of straight lines of the outside world being transformed into curves. Additionally, when the wearer moves his or her eyes, the curves seem to squirm which requires the wearer to hold the eye still and look only through the optical center of such spectacles.

While contact lenses may be superior to the aforementioned spectacles, there are still many problems connected with the wearing of contact lenses to correct aphakic conditions. For example, such contact lenses are very small and fragile and it is difficult to insert and remove them daily. It is also well known that such contact lenses cannot be worn for prolonged periods of time.

In view of the foregoing shortcomings connected with spectacles and contact lenses to correct aphakic conditions, there has been an increasing amount of interest in the use of intraocular lenses that are suitable for use as artificial lens implants to correct aphakic conditions. While the first suggestion of implanting artificial lenses within the eye to obviate the condition of aphakia was probably made by Tardini in 1764, the first actual lens implant was not carried out until 1949 when Dr. Harold Ridley implanted a rather crude intraocular lens. Ridley's first work was centered around the implantation of an intraocular lens in the posterior chamber of the eye behind the iris. This early work of implantation of an intraocular lens in the posterior chamber was abandoned by Ridley because of instances of dislocation after implantation and because of failures associated with glaucoma.

Soon after Ridley's work of limited success with posterior chamber artificial lenses, several others, such as D. P. Choyce, began work with the implantation of intraocular lenses in the anterior chamber of the eye, between the iris and the cornea. The early work in anterior chamber intraocular lenses also met with limited success, mostly because of problems connected with irritation of the eye by the supporting feet or the supporting structure of the intraocular lenses.

Soon after the early work by Ridley and Choyce, surgical techniques for lens implantation were improved by such workers as Drs. C. D. Binkhorst and J. G. F. Worst. The work performed by Binkhorst and Worst developed intraocular lenses that utilized an iris-clip lens and an iridocapsular lens. Both of these types of lens comprise a lens of a larger diameter than the pupil and are placed so that the periphery of the lens engages the front of the iris. The iris-clip lens is held in place by loops which flank the iris and support the lens in front of the pupil. In some instances, the iris is sutured to the clip to secure the positioning of the lens. The iridocapsular lens had two or three loops which protrude from the back of the lens and extend posteriorly behind the iris and engage the capsula of the crystal lens that is left inside the eye after the extracapsular cataract extraction. Both of these early types of intraocular lens met with only limited success because they interferred with the constriction of the pupil and fixed the size of the pupil.

Various other types of intraocular lenses have been suggested and used with varying degrees of success. Such other types of lenses are described in and shown in U.S. Pat. Nos. 3,673,616; 3,906,551; 3,922,728; 3,925,825; 3,971,073; 3,975,779; 3,979,780; 3,986,214; 3,996,627; 4,010,496; 4,056,855; 4,073,015; 4,077,071; 4,079,470; 4,087,866; 4,092,743; 4,174,543; 4,285,072; 4,014,049; 4,053,953; 3,866,249; 4,041,552; 3,913,148 and various technical articles appearing in technical journals and the like.

As a result of the evolution of intraocular lenses, medical science now has progressed to a point where intraocular lenses are used in increasing numbers to correct aphakia. Some of the more widely used and more successful intraocular lenses utilize a design and construction that generally include a light focusing lens body known as an optic that is provided with a support structure known as a haptic. The optic functions to refract light waves in the desired amount to correct the vision of the user. The haptic functions as the fixational element to support and position the intraocular lens apparatus within the eye. In some instances the haptic may be fixed to the natural regions of the eye to align and stabilize the intraocular lens within the eye. All such prior art intraocular lenses are based on the premise that the geometric center axis of the cornea is the desired position for the optical axis of the intraocular lens implant. Therefore, elaborate schemes and structural designs have been devised whereby the intraocular lens can be precisely positioned whereby the optical axis of the lens is positioned precisely at the geometric center of the cornea.

It has now been discovered that the geometric center of the cornea is not the desired or preferred optical axis of the eye. With that discovery, an improved method for correcting vision in humans by the implantation of intraocular lens and improved lens structure has been invented whereby the optical axis of the intraocular lens can be accurately and consistently positioned in the optimum location to restore vision in the human eye when the natural lens of the eye has been removed.

SUMMARY OF THE INVENTION

Accordingly, it is an object of this invention to provide an improved method for the implantation of intraocular lenses to improve and restore normal vision to the human eye when the natural lens of the eye has been removed. It is also an object of this invention to provide an improved intraocular lens that is suitable for implantation into the human eye. It is still another object of this invention to provide an improved intraocular lens that can be used, interchangably, in both the right and left eye of a human whereby the optical axis of the lens can be positioned in the optimum position for restoring sight while the lenses are supported by the natural structure of the eye.

It has been found that improved intraocular lens structure can be provided by constructing a lens that utilizes a light focusing lens body known as the optic with support structure known as the haptic that is supported by the natural regions of the eye to align and stabilize the haptic with respect to the geometric center axis of the cornea but with the optical axis of the lens being offset in either a horizontal or vertical plane from the geometric center of the cornea to correspond to the pupillary axis of the operated eye. Generally, the optical axis of the lenses and methods of this invention will be offset in a horizontal plane from the geometric center axis of the cornea inwardly toward the opposing eye. Identical intraocular lenses can be utilized for both the right and the left eye when the lenses are implanted by rotating the lenses perpendicularly 180° with respect to the optical axis of the lens.

DESCRIPTION OF PREFERRED EMBODIMENTS

The preferred embodiments of this invention can best be described by referring to the attached figures. It should be realized that the figures are not to scale and are presented for illustrative purposes only. In the accompanying drawings.

Figure 1:
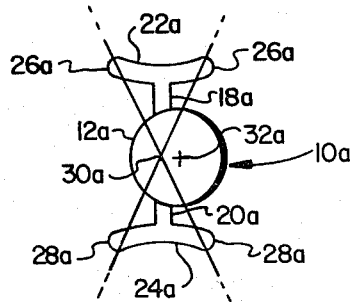
FIGS. 1 through 7 are frontal views of various preferred intraocular lenses in accordance with the present invention.
Figure 2:
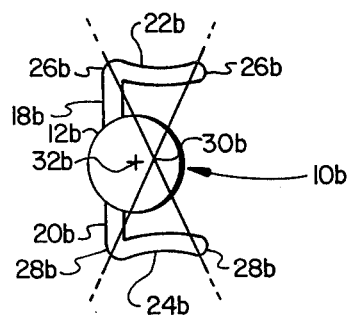
Figure 3:
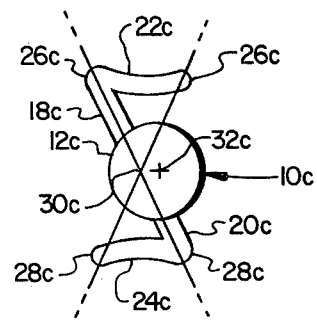
Figure 4:
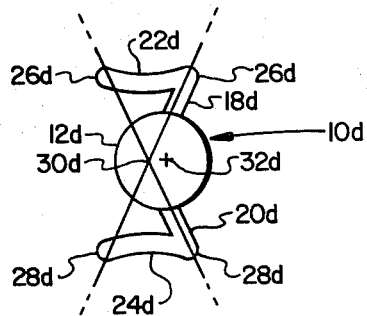
Figure 5:
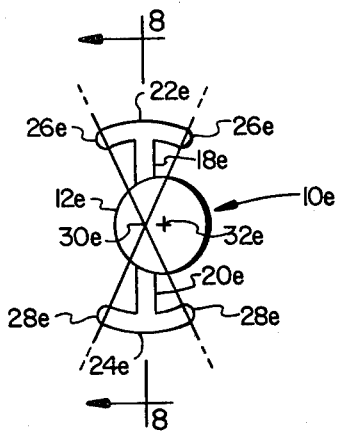
Figure 6:
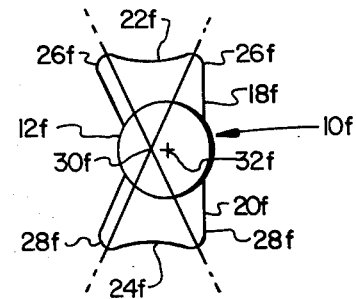
Figure 7:
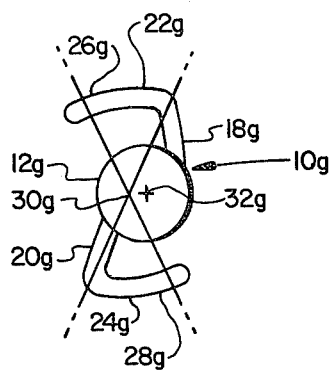
Figure 8:
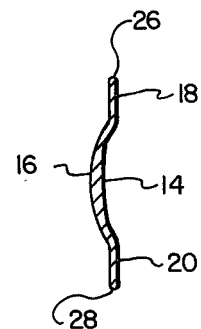
FIG. 8 is a side sectional view of one of the typical preferred intraocular lenses of this invention, such as the lens of FIG. 5, taken along sectional lines 8—8.

By turning to FIGS. 1 through 8, it will be noted that several preferred lens configurations are described. In the detailed explanation of FIGS. 1 through 7, it will be noted that while the appearance of the lenses may differ rather drastically, they all have common features. Therefore, the common features will be described by using common numerals to define the common elements with the variations being defined by letter suffixes. All of the lenses illustrated in FIGS. 1 through 7 are viewed from the frontal or anterior side of the lenses as they would be implanted into a human eye. As will be explained hereafter, the lenses shown in FIGS. 1 and 3 through 6 are oriented for insertion into the right eye and the lens shown in FIG. 2 is oriented for insertion into the left eye. Intraocular lens 10a through 10g generally comprise an optic 12a through 12g which has a generally flat or convex posterior surface 14, as illustrated in FIG. 8 and a generally convex anterior surface 16 as illustrated in FIG. 8. For ease of illustration, FIG. 8 is more particularly defined as a sectional view of FIG. 5, taken along lines 8—8. A pair of oppositely disposed fixation elements, referred to as haptics, extend outwardly from the opposite sides of the optic 12a through 12g. The haptics include stem portions 18a through 18g and 20a through 20g, and limb portions 22a through 22g and 24a through 24g. In FIGS. 1 through 4 and 6, limb portions 22 through 24 terminate with respective contact lobes 26a through 26e and 26g and with contact lobes 28a through 28e and 28g. In FIGS. 5 and 7, contact lobes 26e, 26g, 28e and 28g are continuous lobes along the outer periphery of the limb portions 22e, 22g, 28e and 28g. As will be described hereinafter, the haptics are utilized to properly position the intraocular lens within the human eye with the contact lobes being in contact with the natural structure of the eye to align, position and stabilize the intraocular lenses into the proper location with regard to the geometric center axis of the cornea. It will be appreciated by those skilled in the art that from the aforementioned broad description of the lenses illustrated in FIGS. 1 through 8 such lenses have some structural features that are similar to some prior art lenses. However, the prior art lenses all are constructed with the optical axis of the lenses being positioned precisely at the geometric center axis of the cornea. In FIGS. 1 through 7, the geometric centers of the lenses of this invention are depicted by the intersections of the axis lines which are defined by the oppositely disposed contact lobes 26 and 28. In FIGS. 1 through 7, the geometric centers of the intraocular lenses are depicted at point 30a through 30g. It has been discovered that while points 30a through 30g are the geometric center axis of the cornea, optimum visual efficiency is obtained when the optical axis of the optic 12 is shifted to a point where it is directly aligned with the pupillary axis of the human recipient of the intraocular lens. In FIGS. 1 through 7, the optical axes of the optics 12 are illustrated as 32a through 32g. The geometric axis of an intraocular lens of this invention is generally positioned in the same horizontal plane as the geometric center axis of the cornea with the optical axis being offset to correspond and align with the pupillary axis of the recipient.

It has been found that by utilizing the intraocular lenses of this invention, such lenses can be implanted into a human eye in such a fashion that the lenses are correctly positioned whereby the contact lobes 26 and 28 contact and index with the natural structures of the eye whereby the geometric center of the lenses are positioned precisely in alignment with the geometric center axis of the cornea while the optical axis of the lenses are positioned directly in alignment with the pupillary axis of the human eye. Thus, an isopupillary alignment can be achieved by utilizing the method and lens structure of this invention.

The intraocular lenses of this invention can be made from any material which is biologically inert and is not susceptible to being absorbed by the human fluids and is capable of being tolerated by the human body when implanted and which will retain a highly transparent quality. Such materials which can be used include ophthalmic glass, methylmethacrylate resins, quartz glass, or any other polymeric material meeting the foregoing criteria. Various silicon based polymers can also be utilized. It will be appreciated by those skilled in the art that various known materials can be utilized to form the intraocular lens structures from with such materials being either relatively rigid or relatively flexible. Recently, materials for producing intraocular lens structures have been developed wherein there is a moderate amount of flexibility associated with such lenses whereby such lenses can flex and bend to compensate for various stresses and contortions of the human eye.

Figure 9:
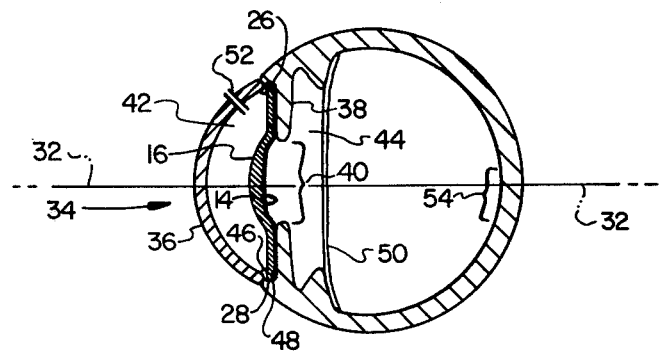
FIG. 9 is a side sectional view of a human eye illustrating the positioning of an anterior chamber intraocular lens implant in accordance with the present invention.

FIG. 9 illustrates the implantation of a preferred embodiment of the present invention wherein an intraocular lens of this invention is implanted into the anterior chamber of a human eye. In FIG. 9, eyeball 34 includes a cornea 36. The geometric center axis of the cornea is depicted by axis line 32 in FIG. 9. Iris 38 defines a circular opening or pupil 40. Annular iris 38 defines a forward or anterior chamber 42 and a posterior chamber 44. Cataract extraction or removal of the natural lens from the eye is normally performed by surgical means through incision 52 which is cut in cornea 36. Scleral spur 46 is an annular inwardly extending flap that lies in a plane roughly parallel to the plane of annular iris 38, thereby forming trabecular meshwork 48 around the interior circumference of the eyeball. Hyloid membrane 50 is disposed behind iris 38 and contains vitreous fluid. The trabecular meshwork is illustrated in the form of annular groove 48 in FIG. 9. The retina of the eye is disposed along the back interior walls of the eyeball and is depicted as region 54. Light entering through cornea 36 must be focused into a sharp image by means of an optical lens onto retina 54 in order for there to be discernable visual perception.

As illustrated in FIG. 9, incision 52 is made into the cornea and the natural lens is removed. Thereafter, the lens of the instant invention is inserted through incision 52. The intraocular lens of this invention is inserted in such a fashion that contact lobes 26 and 28 are seated either in groove 48 or in such other naturally occurring structures of the eyeball whereby the geometric axis 30 of the haptics is accurately aligned with and held in place with the geometric center axis of the cornea. As previously mentioned, however, the geometric axis of the cornea is not at the same point where the optical axis of the pupillary structure exists. By turning to FIGS. 10 and 10a, a view of the right and left eye of a human are graphically illustrated, as viewed from the anterior portions of the eye. It will be noted that the optical axis 32 of the intraocular lenses of this invention are offset from the geometric center of the haptics usually in a direction toward the opposite eye. By utilizing such a configuration, the optical axis of the intraocular lenses of this invention can be positioned precisely in alignment with the pupillary axis of the human eye while the contact lobes 26 and 28 engage and contact the natural structural features of the human eyeball to hold the lens structures in place within the eye.

Figure 10:
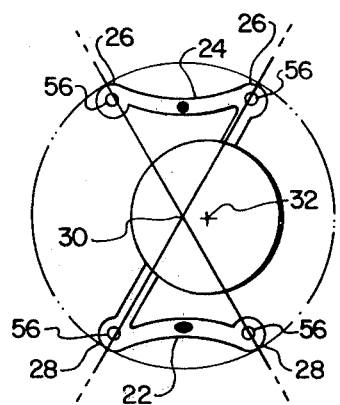
FIGS. 10 and 10a represent a schematic view of intraocular lenses of the present invention as they are implanted in the right and left eyes of a human, illustrating the positioning of the haptics along the geometric axis of the cornea with the offset optical axis of the lens that corresponds to the pupillary axis.
Figure 10A:
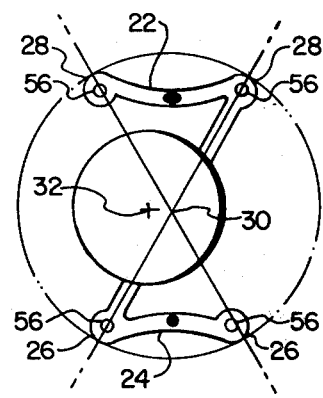

It will be noted that in FIG. 10, the intraocular lens is graphically illustrated as being inserted and implanted into the right eye of a human. In FIG. 10a, an identical lens to that lens which is implanted into the right eye, is implanted into the left eye. However, the lens implant in FIG. 10a has been rotated 180° about the direction perpendicular to the geometric center axis of the cornea. With that in mind, it will be appreciated that one lens design can be made in many different counterparts and that one lens design and configuration can be utilized both for the right eye and the left eye of a human whereby there can be an exact implantation and alignment of the optical axis of the intraocular lens with the pupillary axis simply by rotating the intraocular lens 180° or any amount dictated by the pupillary axis of the eye as the lens is implanted.

For the average human adult, it has been found that the offset of the optical axis of the intraocular lens of this invention from the geometric axis of the lens should be in the order of one millimeter. It will, of course, be appreciated that such dimensions can vary.

It order to facilitate correct implantation of the lenses of this invention, suitable indicia or markings may be made on the lens structure to assist the surgeon in the proper implantation of the lenses. As shown in FIGS. 10 and 10a, circles and ovals have been imprinted on limb portions 22 and 24. Thus, the ophthalmic surgeon can readily detect the orientation of the lenses as he implants such lenses into the human eye. For example, the limb portion marked with a circle can be implanted into the human eye with the circle indicia appearing upright in the right eye and the oval indicia appearing upright in the left eye. Of course, it will be appreciated that such markings and indicia are for convenience only. Other indicia such as dots, color codes, letters and the like can be also utilized for proper installation and implantation of the lenses of this invention.

The implantation procedures are well known in the art. Any suitable means for forming incisions and inserting the intraocular lenses into the human eye can be utilized. It is well known that various surgical tools, such as forceps, lens implantation tools and the like can be utilized for inserting the lenses into the eye. Suitable examples which can be utilized include forceps that engage and index small apertures adjacent the contact lobes. As shown in FIGS. 10 and 10a, such apertures for use with conventional implantation tools are illustrated by means of apertures 56. Such apertures can also be utilized to secure the implanted lenses into place if suturing is desired to hold the lenses in place within the eye.

While it will be appreciated that FIG. 9 shows the cross section of a human eye with the implantation of the intraocular lens in the anterior chamber, such lenses can also be implanted in the posterior chamber.

It will be appreciated that the foregoing descriptions of the methods and structures of this invention are for illustrative purposes only. The foregoing descriptions should in no way be considered to be a detailed surgical procedure but instead are presented to point out and define the important features of this invention. Well known surgical procedures can readily be followed by those skilled in the art in applying the novel methods and implantation of the novel structures of this invention.

The foregoing specification and drawings have been presented to describe the instant invention. It will be appreciated that various changes and modifications may be made in the foregoing specification and drawings without departing from the spirit and scope of this invention.

What is claimed is:

1. An intraocular lens structure suitable for use as an artificial lens implant which comprises a light focusing lens body and a plurality of oppositely disposed support members for supporting said intraocular lens structure upon implantation in the eye, said oppositely disposed support members terminating with a plurality of oppositely disposed contact lobes having intersecting axis lines that define the geometric center of said support members and which are adapted to contact natural regions of the eye upon implantation, to position the intersection of the axis lines which are defined by the oppositely disposed contact lobes in alignment with and corresponding to the geometric center axis of the cornea, said light focusing lens body being affixed to said support members at a position whereby the optical axis of said light focusing lens is offset from said support members geometric center and the geometric center axis of the cornea and whereby said optical axis corresponds with and is in alignment with the pupillary axis.

2. The intraocular lens structure of claim 1 wherein said contact lobes have apertures therein, said apertures being adapted to be engaged by lens implantation tool for inserting said structure into the eye.

3. The intraocular lens structure of claim 1 wherein at least one of said oppositely disposed support members had indicia thereon to indicate orientation of said structure.

4. A method for correcting aphakic conditions in the human eye which comprises implanting an intraocular lens structure within the eye wherein said intraocular lens comprises a light focusing lens body and a plurality of oppositely disposed support members for supporting said lens body upon implantation, said oppositely disposed support members terminating with a plurality of oppositely disposed contact lobes having intersecting axis lines defining the geometric center of said support members which contact natural regions of the eye upon implantation to position the intersection of the axis lines which are defined by the oppositely disposed contact lobes in alignment with and corresponding to the geometric center axis of the cornea with said light focusing lens body being affixed to said support members at a position whereby the optical axis of said light focusing lens is offset from said support members geometric center and the geometric center axis of the cornea and whereby said optical axis corresponds with and is in alignment with the pupillary axis of the eye.

5. The method of claim 4 wherein said intraocular lens is implanted in the anterior chamber of the eye.

6. The method of claim 5 wherein said support members contact and are supported by the trabecular meshwork of the eye.

7. A method of correcting aphakic conditions in human eyes which comprises:
(a) implanting intraocular lens structures within the eyes wherein said intraocular lens structures have a light focusing body which is supported by a plurality of oppositely disposed support members wherein said oppositely disposed support members terminate with contact lobes having intersecting axis lines defining the geometric center of said support members which are adapted to contact natural regions of the eye upon implantation to position the intersection of the axis lines which are defined by the oppositely disposed contact lobes in alignment with and corresponding to the geometric center axis of the cornea with the optical axis of said light focusing lens body being offset from said support members geometric center and the geometric center axis of the cornea and
(b) rotating said intraocular lens structure in a plane perpendicular to the geometric center axis of the cornea to a point where the optical axis of said light focusing body is in alignment with and corresponds to the pupillary axis of the eye.

8. The method of claim 7 wherein said intraocular lens structure is implanted in the anterior chamber of the eye.

9. The method of claim 8 wherein the terminal portions of said support members contact and are supported by the trabecular meshwork of the eye.

* * * * *